United States Patent
Kitagawa

(10) Patent No.: US 7,550,081 B2
(45) Date of Patent: Jun. 23, 2009

(54) MOBILE PHASE SUPPLYING APPARATUS, LIQUID CHROMATOGRAPH USING THE SAME, AND MOBILE PHASE SUPPLYING METHOD

(75) Inventor: Takaei Kitagawa, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 284 days.

(21) Appl. No.: 11/378,193

(22) Filed: Mar. 17, 2006

(65) Prior Publication Data
US 2006/0213837 A1 Sep. 28, 2006

(30) Foreign Application Priority Data
Mar. 25, 2005 (JP) .............................. 2005-087803

(51) Int. Cl.
*B01D 15/08* (2006.01)
(52) U.S. Cl. .................... 210/198.2; 210/101; 210/143; 210/659
(58) Field of Classification Search .............. 210/198.2, 210/656, 659, 101, 143
See application file for complete search history.

(56) References Cited

U.S. PATENT DOCUMENTS

| | | | | |
|---|---|---|---|---|
| 4,239,623 A | * | 12/1980 | Schrenker | 210/96.1 |
| 4,595,495 A | * | 6/1986 | Yotam et al. | 210/101 |
| 4,595,496 A | * | 6/1986 | Carson | 210/101 |
| 4,882,063 A | * | 11/1989 | Allington et al. | 210/659 |
| 5,080,785 A | * | 1/1992 | Allington et al. | 210/198.2 |
| 5,360,320 A | * | 11/1994 | Jameson et al. | 417/4 |
| 5,468,643 A | * | 11/1995 | Su et al. | 436/161 |
| 6,780,315 B2 | * | 8/2004 | Richardson et al. | 210/198.2 |
| 6,793,815 B2 | * | 9/2004 | Hoffmann | 210/198.2 |
| 6,860,137 B2 | * | 3/2005 | Kitagawa | 73/1.02 |
| 7,141,161 B2 | * | 11/2006 | Ito | 210/198.2 |
| 7,186,336 B2 | * | 3/2007 | Gerhardt et al. | 210/198.2 |
| 2004/0108273 A1 | * | 6/2004 | Richardson et al. | 210/656 |
| 2005/0098487 A1 | * | 5/2005 | Ito | 210/101 |
| 2006/0213837 A1 | * | 9/2006 | Kitagawa | 210/656 |
| 2006/0219618 A1 | * | 10/2006 | Witt et al. | 210/198.2 |
| 2007/0034557 A1 | * | 2/2007 | Ito | 210/101 |

FOREIGN PATENT DOCUMENTS

JP 2003-98166 4/2003

OTHER PUBLICATIONS

PTO Translation No. 2006-3692 of Japan Patent No. 2002-98155 pp. 1-48 Apr. 2006.*

* cited by examiner

*Primary Examiner*—Ernest G Therkorn
(74) *Attorney, Agent, or Firm*—Rankin, Hill & Clark LLP

(57) ABSTRACT

In liquid-feeding sections for feeding two types of mobile phases A, B, respectively, actual flow rate measuring sections capable of detecting back-flows are provided in downstream of liquid-feeding pumps, respectively. Control devices control driving of the liquid feeding pumps, respectively, so that measured flow rates by the actual flow rate measuring sections correspond to set flow rates on the liquid-feeding flow paths, respectively. In a case where the set flow rate is zero, when either of the actual flow rate measuring sections detects the back-flow, the corresponding liquid-feeding pump is driven so as to prevent the back-flow.

1 Claim, 3 Drawing Sheets

MOBILE PHASE SUPPLYING APPARATUS, LIQUID CHROMATOGRAPH USING THE SAME, AND MOBILE PHASE SUPPLYING METHOD

This application claims foreign priority based on Japanese Patent application No. 2005-087803, filed Mar. 25, 2005, the content of which is incorporated herein by reference in its entirety.

BACKGROUND OF THE INVENTION

1. Field of the Invention

This invention relates to a liquid chromatograph including a mobile phase supplying apparatus of a high-pressure gradient system, the mobile phase supplying apparatus supplying mobile phases while controlling a composition of the mobile phases, the mobile phase supplying apparatus having a plurality of liquid-feeding pumps for feeding the mobile phases, respectively, a plurality of liquid-feeding flow paths having the liquid-feeding pumps, respectively, a mixer for mixing the mobile phases by merging the liquid-feeding flow paths; at least one control device for controlling a driving of each of the liquid-feeding pumps based on a flow rate being set. This invention also relates to a liquid chromatograph including a high-speed liquid chromatograph using the mobile phase supplying apparatus. This invention also relates to a mobile phase supplying method in the liquid chromatograph including the mobile phase supplying apparatus.

2. Description of the Related Art

FIG. 4 shows a liquid chromatograph equipped with a related mobile phase supplying apparatus of a high-pressure gradient system.

Liquid-feeding pumps 10, 14 are provided respectively in liquid-feeding flow paths 2, 4 for feeding mobile phases A, B. Each of the liquid-feeding pumps 10, 14 controls a liquid-feeding amount (an amount of liquid to be fed) by controlling a number of revolutions of a motor. The liquid-feeding flow paths 2, 4 are merged by a mixer 18. The mixer 18 mixes the mobile phases A and B to be fed into a flow path 20 for analysis. A separating column 24 is provided through an injector (sample injecting section) 22 in the analysis flow path 20. A detector 26 is provided in downstream of the separating column 24.

A sample injected from the injector 22 is led to the separating column 24 by the mobile phases mixed by the mixer 18, and separated into respective constituents. The separated constituents of the sample are detected by the detector 26.

The liquid-feeding amounts of the liquid-feeding pumps 10, 14 are respectively controlled by a control device 19a so that the liquid-feeding amounts are changed according to a certain liquid-feeding program.

Using such a liquid chromatograph, as seen from FIG. 5A, an analysis is started from a liquid-feeding state in which a percentage of the mobile phase A liquid is 100% and a percentage of the mobile phase B liquid is 0%. Then, concentration of the mobile phase A liquid is gradually reduced whereas concentration of the mobile phase B liquid is gradually increased. Eventually, the percentage of the mobile phase A liquid is changed to 0% and the percentage of the mobile phase B liquid is changed to 100%. Thus, the sample is analyzed while a retention amount of the sample in the column 24 is changed. Such analysis is called a gradient analysis method. Particularly, the gradient system in which the plurality of the liquid-feeding pumps is used and the plurality of the mobile phases is merged on the downstream side of the liquid-feeding pumps is called a high-pressure gradient system (for example, refer to JP-A-2003-98166). In FIGS. 5A and 5B, A and B in the vertical axis represent that the percentage of A liquid is 100% and the percentage of B liquid is 100%, respectively. The horizontal axis represents time.

In the related mobile phase supplying apparatus having the configuration shown in FIG. 4, for example, in the liquid-feeding state in which the percentage of the mobile phase A liquid is 100% and the percentage of the mobile phase B liquid is 0% before the start of the analysis, or in the liquid-feeding state in which the percentage of the mobile phase A liquid is 0% and the percentage of the mobile phase B liquid is 10%, one of the two liquid-feeding pumps 10 and 14 on a side in which the percentage of the mobile phase is 0% remains in a drive-stopped state. In a general gradient analysis, before the start of the analysis, the state at this time (in this case, the liquid-feeding state in which the percentage of the mobile phase A liquid is 100% and the percentage of the mobile phase B liquid is 0%) is maintained for a while so as to stabilize a state in the separating column 24.

Assuming that in the state before the start of the analysis, the percentage of the mobile phase A liquid is 100% and the percentage of the mobile phase B liquid is 0%, while the state before the start of the analysis is maintained, airtightness in the liquid-feeding pump 14 which remains stopped cannot be completely maintained. Thus, the mobile phase A liquid on the liquid-feeding side is pushed out toward the liquid-feeding pump 14, which causes a back-flow of the mobile phase A liquid. When an amount of the back-flow is large, even when the liquid-feeding pump 14 starts to feed the liquid after the start of the analysis, the mobile phase B liquid is not fed for the amount of the back-flow at first. Thus, as shown in FIG. 5B, arise of the gradient is poor, and accurate analysis cannot be performed. The same also applies to the case where in the state before the start of the analysis, the percentage of the mobile phase B liquid is 100% and the percentage of the mobile phase A liquid is 0%.

SUMMARY OF THE INVENTION

An object of the invention is to provide a mobile phase supplying apparatus and a mobile phase supplying method of a high-pressure gradient system capable of solving the above problem related to the rise of the gradient, and a liquid chromatograph using the mobile phase supplying apparatus.

In some implementations, a mobile phase supplying apparatus of the invention of a high-pressure gradient system for supplying mobile phases while controlling a composition of the mobile phases, the mobile phase supplying apparatus comprises: a plurality of liquid-feeding pumps for feeding the mobile phases, respectively; a plurality of liquid-feeding flow paths having the liquid-feeding pumps, respectively; a mixer for mixing the mobile phases by merging the liquid-feeding flow paths; at least one control device for controlling driving of each of the liquid-feeding pumps based on flow rates being set for the respective liquid-feeding flow paths; and a plurality of actual flow rate measuring sections for measuring actual flow rates in the liquid-feeding flow paths respectively, each of the actual flow rate measuring sections being provided in downstream of the liquid-feeding pump in each of the liquid-feeding flow paths, wherein when the control device determines that a back-flow exists in the liquid-feeding flow path of which set flow rate is zero based on the measured actual flow rate, the control device controls the driving of the liquid-feeding pump in said liquid-feeding flow path so as to cancel the back-flow.

When the back-flow of the mobile phase is detected in the liquid-feeding flow path while the set flow rate being zero, the operation of feeding a minute amount of liquid for canceling the back-flow is performed.

In some implementations, a liquid chromatograph of the invention comprises: the mobile phase supplying apparatus of the invention; a sample injecting section being provided in downstream of the mobile phase supplying apparatus in a flow path for analysis where the mobile phases are supplied from the mobile phase supplying apparatus; a separating column for separating an injected sample into its constituents, the separating column being provided in downstream of the sample injecting section; and a detector for detecting each of the constituents separated by the separating column.

In the mobile phase supplying apparatus according to this invention, the back-flow can be also detected in the actual flow rate measuring section in each of the liquid-feeding flow paths so that when the back-flow is detected in the liquid-feeding flow path of which set flow rate is zero, the liquid-feeding pump is driven to prevent the back-flow. Thus, the back-flow of the mobile phase is prevented in the liquid-feeding flow path in which the liquid feeding is stopped, thereby improving the rise of the gradient.

The liquid chromatograph according to this invention includes the mobile phase supplying apparatus according to this invention. For this reason, the back-flow of the mobile phase is prevented so as to improve the rise of the gradient. Therefore, an accurate analysis can be realized. Particularly, in a micro LC (liquid chromatograph) or nano LC in which a liquid-feeding flow rate of the mobile phase is very small such as µL/minute or nL/minute, and the influence of the back-flow is large, this invention is more effectively employed.

DESCRIPTION OF THE PRFERRED EMBODIMENTS

Figure 1:
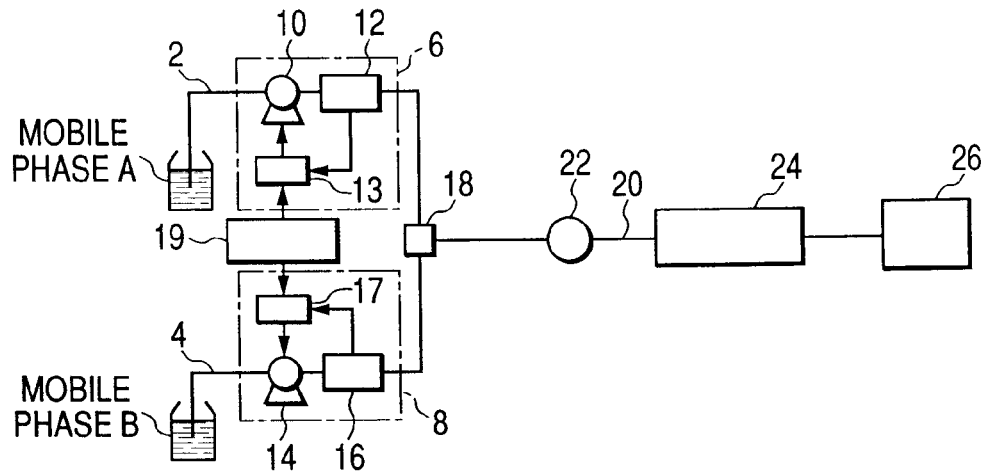
FIG. 1 is a flow-path diagram showing a configuration of a liquid chromatograph according to an embodiment of the invention.

Now referring to the drawings, an explanation will be given of an embodiment of a liquid chromatograph provided with a mobile phase supplying apparatus according to this invention.

FIG. 1 is a flow-path diagram showing the liquid chromatograph. In this embodiment, two types of mobile phases such as A and B liquids are mixed and fed. However, this invention is limited to such a configuration, and can be similarly applied to a mobile phase supplying apparatus in the gradient system in which three or more types of mobile phases are mixed and fed.

The two types of the mobile phases A and B are fed to a mixer 18 through corresponding liquid-feeding flow paths 2, 4, and mixed in the mixer 18. A liquid-feeding section 6 is provided in the liquid-feeding flow path 2 for feeding the liquid A, and a liquid-feeding section 8 is provided in the liquid-feeding flow path 4 for feeding the liquid B.

The liquid-feeding section 6 includes a liquid-feeding pump 10, an actual flow rate measuring section 12 provided in downstream of the liquid-feeding pump 10 so as to measure an actual flow rate of the liquid fed by the liquid-feeding pump 10, and a control device 13 for controlling a driving of the liquid-feeding pump 10 based on a set flow rate. The liquid-feeding section 8 has also the same configuration, that is, the liquid-feeding section 8 includes a liquid-feeding pump 14, an actual flow rate measuring section 16 provided in downstream of the liquid-feeding pump 14 so as to measure an actual flow rate of the liquid fed by the liquid-feeding pump 14, and a control device 17 for controlling a driving of the liquid-feeding pump 14 based on a set flow rate.

The actual flow rate measuring sections 12, 16 can detect a back-flow. The control devices 13, 17 respectively control the driving of the corresponding liquid pumps 10, 14 so that the flow rates in the corresponding liquid-feeding flow paths 2, 4 respectively become equal to the set flow rates.

The liquid-feeding pumps 10, 14 feed the liquid while rotating driving motors respectively. Each of the liquid-feeding pumps 10, 14 may be a pump of a plunger reciprocating type, for example, including a cam connected to the driving motor, a plunger which performs a reciprocating movement with its end portion being in contact with an outer periphery of the cam, and a pump head which performs suction and discharge of the mobile phase through the reciprocating movement of the plunger. The liquid-feeding amounts of the liquid-feeding pumps 10, 14 depend on numbers of revolutions of the motors respectively.

As the actual flow rate measuring sections 12, 16 which also can detect the back-flow, any one of various systems may be employed such as a system which measures the flow rate by heating a center of the flow path by a heater, and measuring temperature gradient between upstream and downstream sides of the heater, and another system which measures the flow rate by installing a small water turbine in the flow path, and measuring a rotary speed of the water turbine.

Reference numeral 19 denotes a flow rate setting section for setting the set flow rates in the control devices 13, 17 in the liquid-feeding flow paths 2, 4 respectively in accordance with a gradient program for gradient analysis, or by a direct setting by a user.

In an analysis flow path 20 on which the mobile phases mixed by the mixer 18 are fed for analysis, an injector (sample injecting section) 22, a separating column 24 in downstream of the injector 22 and a detector 26 in downstream of the separating column are provided. The injector 22 injects a sample into the analysis flow path 20, the separating column 24 separates the sample injected from the injector 22 into its constituents, and the detector 26 detects the constituents of the sample being eluted by being separated in the separating column 24.

Figure 2:
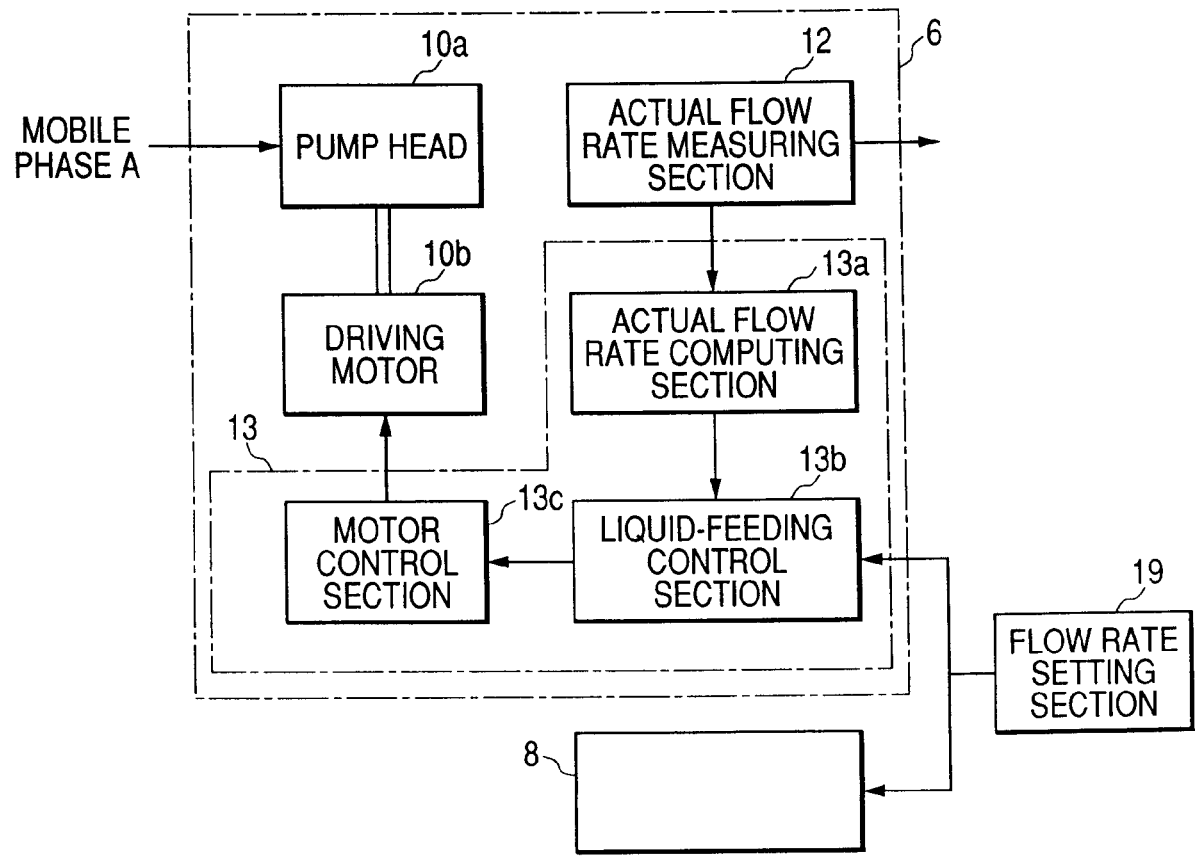
FIG. 2 is a block diagram showing a mobile phase supplying apparatus according to an embodiment of the invention.

The details of the liquid-feeding sections 6, 8 are shown in FIG. 2. Since the liquid-feeding sections 6, 8 have the same configuration, only the liquid-feeding section 6 is shown in details, and the liquid-feeding section 8 is shown as a single block.

The liquid-feeding pump 10 includes a pump head 10a, and a driving motor 10b for driving the pump head 10a. In the mobile phase flow path from the pump head 10a, the actual flow rate measuring section 12 is provided.

Reference numeral 13a denotes an actual flow rate computing section which fetches a signal from the actual flow rate measuring section 12 to compute the flow rate. Reference numeral 13b denotes a liquid-feeding control section which controls the number of revolutions of the motor 10b by a motor control section 13c based on a set value in a flow rate setting section 19. By controlling the rotation of the driving motor 10b through the motor control section 13c, the mobile phase is fed by the pump head 10a with a certain flow rate.

A control device 13 includes the actual flow rate computing section 13a, the liquid-feeding control section 13b and the motor control section 13c. The control device 17 also has the same configuration.

The control devices 13, 17 and the flow rate setting section 19 are configured with a CPU or the like, respectively. In this embodiment, the corresponding control devices are provided in the liquid-feeding flow paths 2, 4, respectively. However, the control devices 13, 17 maybe unified into a single device, otherwise these control devices and the flow rate setting section 19 may be realized by a single CPU. Further, functions for the liquid-feeding flowpaths 2, 4 maybe realized by programs respectively.

Figure 3:
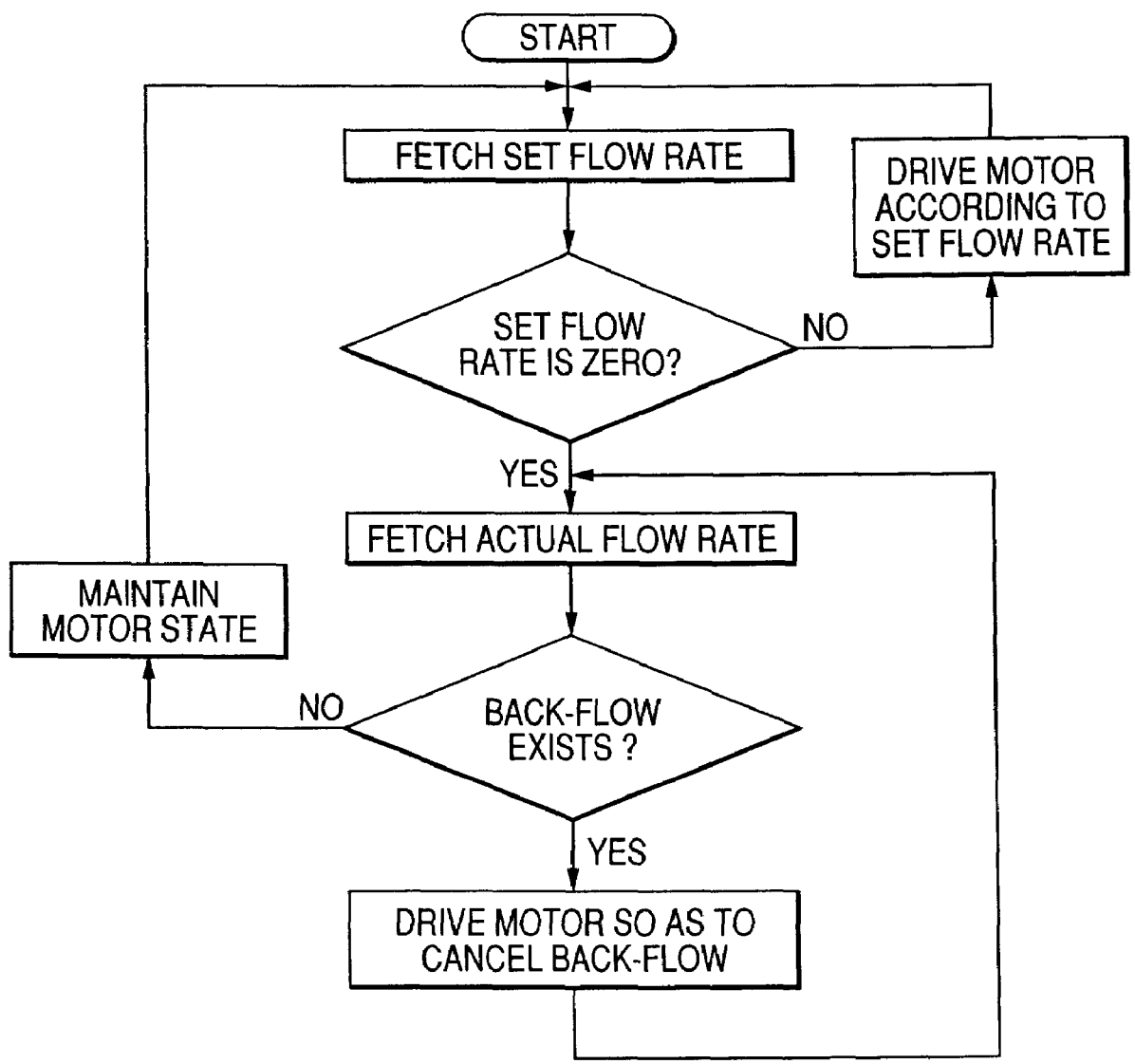
FIG. 3 is a flowchart showing an operation in an embodiment of the invention.
Figure 4:
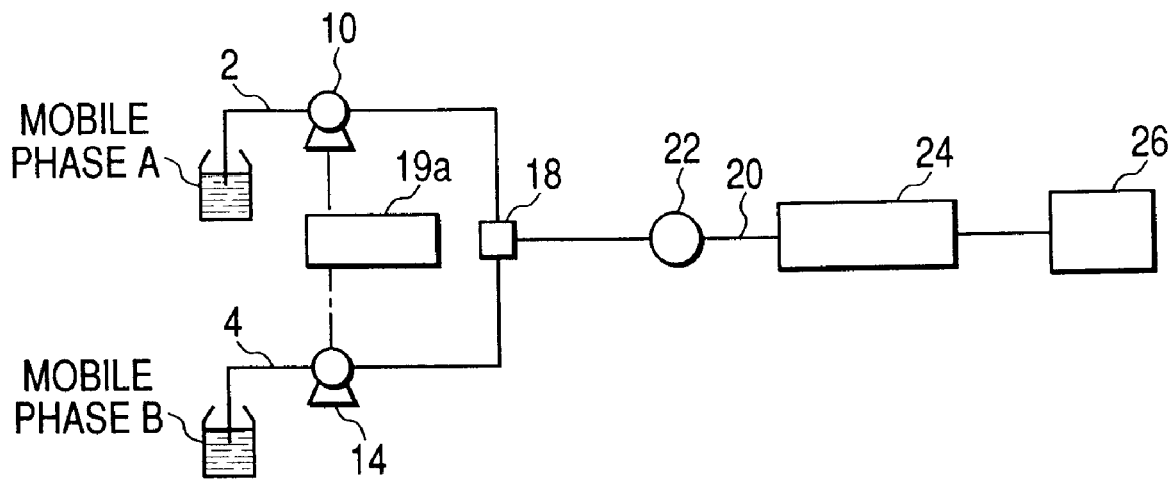
FIG. 4 is a flow-path diagram showing a related liquid chromatograph.
Figure 5A:
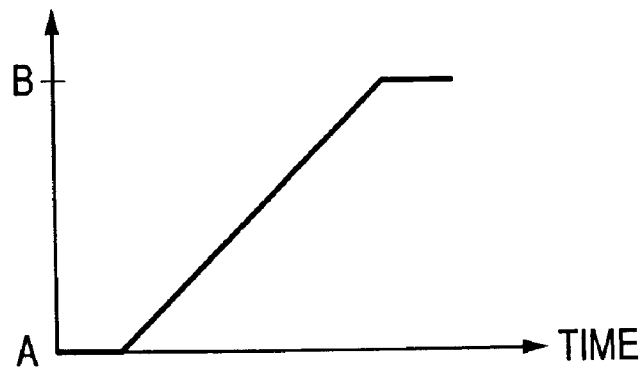
FIGS. 5A and 5B are graphs respectively showing change in composition of mobile phases in a gradient operation.
Figure 5B:
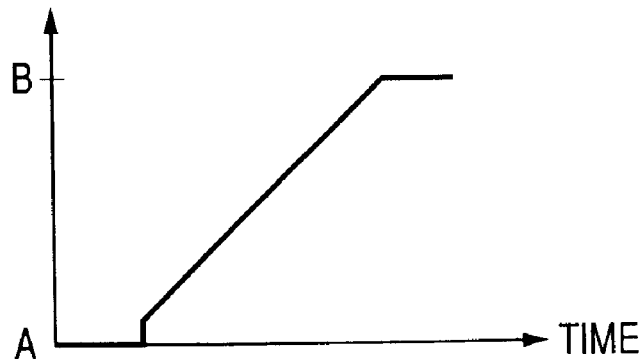

A control of the flow rate by the control device 13 is shown in FIG. 3.

First, the liquid-feeding control section 13b fetches the set value in the flow rate setting section 19. Then, when the set flow rate is not zero, the liquid-feeding control section 13b rotates the driving motor 10b by the number of revolutions corresponding to the set flow rate through the motor control section 13c. The mobile phase is fed from the liquid-feeding pump according to the number of revolutions.

When the flow rate of the liquid-feeding flow path 2 is set at zero by the flow rate setting section 19, the rotation of the driving motor 10b is stopped. At this time, whether or not the actual flow rate is zero is checked by the actual flow rate measuring section 12. The actual flow rate measuring section 12 can detect the back-flow. In the actual flow rate measuring section 12 in the liquid-feeding flow path 2, in the case where a mechanism for measuring the temperature gradient due to the heating by the heater is employed, when the temperature gradient becomes opposite to that in normal liquid-feeding, it is estimated that there is the back-flow. In the case where it a mechanism of a minute water turbine is employed, when the rotating direction becomes opposite to that in the normal liquid-feeding, it is estimated that there is the back-flow. In this way, when the actual flow rate computing section 13a determines that there is the back-flow, this is reported to the liquid-feeding control section 13b. Correspondingly, the liquid-feeding control section 13b gives the number of revolutions of the motor that is enough to cancel the back-flow rate to the driving motor 10b by the motor control section 13c. Thus, while the actual flow rate is being measured, the number of revolutions of the motor is controlled until the actual flow rate becomes zero. When the actual flow rate becomes zero, the number of revolutions of the driving motor 10b is maintained.

In the other liquid-feeding section 8, in entirely the similar way, the number of revolutions of the driving motor (not shown) in the liquid-feeding pump 14 is controlled. Thus, the driving motor of the liquid-feeding pump 14 is driven according to the set flow rate, and the back-flow when the set flow rate is zero is prevented.

As described above, since the mechanism of the flow rate control operates in a closed loop, the state in which the back-flow does not exist and the liquid-feeding is not performed is realized by a feedback control.

The mobile phase supplying apparatus according to this invention can be applied to a liquid chromatograph of a high-pressure gradient system in which an analysis is performed while changing the composition of the mobile phases.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A liquid chromatograph comprising:
a mobile phase supplying apparatus of a high-pressure gradient system configured to supply mobile phases while controlling a composition of the mobile phases, the mobile phase supplying apparatus comprising:
a plurality of liquid-feeding pumps configured to feed the mobile phases, respectively;
a plurality of liquid-feeding flow paths having the liquid-feeding pumps, respectively;
a mixer configured to mix the mobile phases by merging the liquid-feeding flow paths;
at least one control device configured to control driving of each of the liquid-feeding pumps based on flow rates being set for the respective liquid-feeding flow paths;
a plurality of actual flow rate measuring sections provided downstream of the liquid feeding pump in each liquid-feeding flow path, the plurality of actual flow rate measuring sections configured to measure an actual flow rate and to detect a back-flow in the corresponding liquid-feeding flow path; and
a plurality of actual flow rate computing sections configured to compute an actual flow rate in the corresponding liquid feeding flow path;
a sample injecting section provided downstream of the mobile phase supplying apparatus in a flow path for analysis where the mobile phases are supplied from the mobile phase supplying apparatus;
a separating column for separating an injected sample into its constituents, the separating column provided downstream of the sample injecting section; and
a detector for detecting each of the constituents separated by the separating column,
wherein when one of the plurality of actual flow rate measuring sections detects a back-flow in the corresponding liquid-feeding flow path, the corresponding actual flow-rate computing section computes an actual back-flow rate and outputs a signal to the corresponding control device,
wherein the corresponding control device controls the corresponding liquid-feeding pump so as to cancel the back-flow based on the computed actual flow rate.

* * * * *